(12) United States Patent
Henley

(10) Patent No.: US 11,130,942 B2
(45) Date of Patent: Sep. 28, 2021

(54) DEVICE AND SURGICAL SYSTEM FOR RAPID ASEPTIC ISOLATION AND CONCENTRATION OF AUTOLOGOUS FAT DERIVED STEM CELLS

(71) Applicant: Julian Henley, Fort Collins, CO (US)

(72) Inventor: Julian Henley, Fort Collins, CO (US)

( * ) Notice: Subject to any disclaimer, the term of this patent is extended or adjusted under 35 U.S.C. 154(b) by 218 days.

(21) Appl. No.: 16/225,455

(22) Filed: Dec. 19, 2018

(65) Prior Publication Data

US 2019/0119646 A1    Apr. 25, 2019

Related U.S. Application Data

(63) Continuation of application No. 15/016,561, filed on Feb. 5, 2016, now Pat. No. 10,196,611.

(60) Provisional application No. 62/113,425, filed on Feb. 7, 2015.

(51) Int. Cl.
| | |
|---|---|
| *A61K 35/28* | (2015.01) |
| *C12N 5/0775* | (2010.01) |
| *C12N 13/00* | (2006.01) |
| *C12M 1/12* | (2006.01) |
| *C12M 1/33* | (2006.01) |
| *A61K 35/35* | (2015.01) |

(52) U.S. Cl.
CPC ............ *C12N 5/0667* (2013.01); *A61K 35/28* (2013.01); *A61K 35/35* (2013.01); *C12M 25/14* (2013.01); *C12M 45/02* (2013.01); *C12N 13/00* (2013.01); *C12N 2509/10* (2013.01)

(58) Field of Classification Search
USPC ............................................... 607/5; 600/567
See application file for complete search history.

(56) References Cited

U.S. PATENT DOCUMENTS

| | | | |
|---|---|---|---|
| 5,823,990 A | 10/1998 | Henley | |
| 2011/0282242 A1* | 11/2011 | Cronin | A61B 10/0275 600/567 |

* cited by examiner

*Primary Examiner* — Nicole F Lavert
(74) *Attorney, Agent, or Firm* — Polsinelli PC

(57) ABSTRACT

The present disclosure provides an apparatus for harvesting stem cells from fat tissue. The apparatus may include a first transducer coupled to a first end of an resonant horn to form an ultrasonic resonator. The resonant horn may include an elongated body having a plurality of through-holes configured to accommodate a plurality of specimen containers that are positioned substantially perpendicular to the elongated body. The apparatus may also include a wave generator coupled to the first transducer to generate an ultrasonic wave, wherein the elongated body has a length that is multiples of the half-wavelength of the ultrasonic wave.

20 Claims, 6 Drawing Sheets

DEVICE AND SURGICAL SYSTEM FOR RAPID ASEPTIC ISOLATION AND CONCENTRATION OF AUTOLOGOUS FAT DERIVED STEM CELLS

CROSS-REFERENCES TO RELATED PATENT APPLICATIONS

This application is a continuation application of U.S. application Ser. No. 15/016,561 filed Feb. 5, 2016, now U.S. Pat. No. 10,196,611, which application claims priority to U.S. Patent Application No. 62/113,425, entitled "Device and Surgical System for Rapid Aseptic Isolation and Concentration of Autologous Fat Derived Stem Cells," filed on Feb. 7, 2015. Both applications are incorporated herein by reference in their entireties.

FIELD

The present disclosure is directed to devices and methods for extraction of stem cells from a harvested fat sample from a patient and the reintroduction of the extracted stem cells into the patient. The entire procedure of extraction is sterile, fast, and cost effective.

BACKGROUND

Stem cell research and interest has been accelerating in recent years since methods of identification have been developed. Certain stem cells within the body have the potential to differentiate under proper environment into different cell lines. The stem cells, that are able to differentiate under proper environment into different cell lines, are generally dispersed in many tissues and not readily identifiable in vivo nor readily concentrated for clinical applications outside sophisticated cellular laboratories. There has been an increasing interest in medical applications and hope of promoting healing of damaged organs and regenerating tissue in areas like damaged hearts, kidney, or even nerves. Nerve tissue damage is often devastating to the individual until recently, as the nerve tissue damage has been thought as non-repairable. The stem cells have been found in embryos and umbilical cord blood. However, such sources were challenged by ethical issues and issues of antigenic compatibility between donor and recipient cell lines. In more recent years, autologous sources of pleuro-potential cells were found in bone marrow, blood, and fat. For autologous applications, blood, bone marrow, and fat offer a readily accessible tissue with minimal morbidity in harvesting the stem cells.

When the fat tissue is broken down, the lipid containing component is removed. The residual is referred to as a stromovascular component that contains numerous mesenchymal derived pluripotential cells. The stromovascular component including concentrated stromaovascular cells, which are of great interest for their potential in tissue regeneration in variety of degenerative clinical conditions such as osteoarthritis, chondromalacia, cardiovascular, and neurological conditions. Numerous studies also suggest that the regional effect of surrounding tissue in need of repair plays a role in cellular differentiation as well as circulating factors described as growth factors.

Existing approaches in autologous concentration of fat derived stem cells, also referred to as a stromovascular layer or component, are based on enzymatic breakdown of supportive structures and small vessels were the pleuro-potential cells are thought to reside within fat. Protocols for clinical use harvest stromaovascular cells or stem cells from fat tissue of a patient, and subject the fat tissue to an enzymatic breakdown, followed by a centrifuge cycle to extract the stromovascular component or stromaovascular cells, and then mixing the stromovascular component with Platelet Rich Plasma (PRP) derived from blood to contain a variety of stimulating growth factors. Some approaches also subject the mixture of stromovascular component with PRP to light stimulation/activation of underlying peptide factors before reinsertion of the mixture into the patient. Recent studies in Korea and UCLA identify a subset of pleuro-potential cells within fat called Muse-AT that appear to have greater differentiation and repair capability than other mesenchymal derived cells.

The conventional process not only introduces reagents to the fat sample, but also has challenges in proper processing and retention of sterility if such stromovascular cells were to be re-injected into the same patient. Specifically, by using collagenase or similar enzymes to breakdown the supportive structures in fat tissue or fat sample, followed by centrifugation, the stromovascular cells can be concentrated and used in numerous emerging clinical applications. The above extraction for a viable stromovascular component from fat tissue is generally a cumbersome laboratory process, which introduces enzymatic components and also includes manual handling steps that challenge the sterility of the stromovascular component that is reintroduced into the patient, if the intent is to graft the processed stromovascular component back to the patient from whom a fat tissue is collected and the cells are harvested from the fat tissue.

There is a rapidly expanding interest in developing autologous stem cell treatments for various disorders affecting mankind. However, a rapid, cost effective, safe, and bedside device has yet not been developed. Accordingly, there is a need in developing the device and system described hereforth.

BRIEF SUMMARY

The present disclosure provides devices and methods that allow clinicians to rapidly extract a stromovascular component or stromovascular cells from a surgically harvested fat sample. These stromovascular cells are viable, autologous, and sterile after completion of the extraction process. These laboratory devices can be readily completed by any support staff in a clinical facility or point of care without any specialized laboratory training. The device does not include any direct specimen handling that may inadvertently impact sterility. In an embodiment, an apparatus is provided for harvesting stem cells from fat tissue. The apparatus may include a first transducer coupled to a first end of an resonant horn to form an ultrasonic resonator. The resonant horn may include an elongated body having a plurality of through-holes configured to accommodate a plurality of specimen containers that are positioned substantially perpendicular to the elongated body. The apparatus may also include a wave generator coupled to the first transducer to generate an ultrasonic wave, wherein the elongated body has a length that is multiples of the half-wavelength of the ultrasonic wave.

In an embodiment, an apparatus is provided for extracting stem cells from fat tissue. The apparatus may include a specimen container having a closed bottom and an open top. The apparatus may also include an electromechanical agitator inside the specimen container. The apparatus may further include an agitator cap removably coupled and sealed to the electromechanical agitator and configured to seal the top of the specimen container to maintain specimen sterility. The apparatus may also include an aspiration cap removably coupled and sealed to the specimen container to maintain specimen sterility, the aspiration cap including a syringe with a fluid channel for specimen extraction from the specimen container.

In an embodiment, a method is provided for sterilely extracting stem cells from fat. The method may include placing a specimen container containing fat in an ultrasonic resonator and applying an external ultrasonic field to the fat to separate stem cells from the fat in a medical care room. The method may also include placing the specimen container in a centrifuge to concentrate the separated stem cells and removing the specimen container from the centrifuge. The method may further include extracting the concentrated stem cells from the specimen container. The specimen retains sterility through the sequence of the above steps.

In an embodiment, a method is provided for extracting stem cells from fat. The method may include placing an agitator cap onto an open end of a specimen container having an open end and closed bottom. The agitator cap may be removably coupled to the specimen container and also coupled to a mechanical agitator. The method may also include separating stem cells from fat in a specimen container by the mechanical agitator in an operating sterile room. The method may further include replacing the agitator cap with an aspiration cap onto the open end of the specimen container. The aspiration cap may be removably coupled to the specimen container and also coupled to a syringe configured for extracting samples from the specimen container. The method may also include placing the specimen container with the aspiration cap in a centrifuge to concentrate the separated stem cells, removing the specimen container from the centrifuge, and followed by extracting the stem cells from the bottom of the specimen container. The specimen retains sterility through the sequence of the above steps.

In an embodiment, a method is provided for extracting stem cells from fat. The method may include getting a fat sample from a patient using a syringe with vacuum assistance and electromechanically agitating the fat sample in a tube with a sealed cap in a medical care room. The method may also include centrifuging the agitated fat sample in a sealed tube to retain sterility. The method may further include extracting the structural fraction containing stem cells from the tube in the medical care room, and reintroducing the stem cells to the same patient in the medical care room.

In an embodiment, a method is provided for extracting stem cells from fat tissue. The method may include agitating the fat tissue in a sealed container to produce a stromovascular component containing stem cells. The method may also include centrifuging the sealed container to concentrate the stromovascular component. The method may further include extracting the concentrated stromovascular component from the sealed container. The fat tissue and the stromovascular component remain sterility in the sealed container.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein.

DETAILED DESCRIPTION

Figure 1:
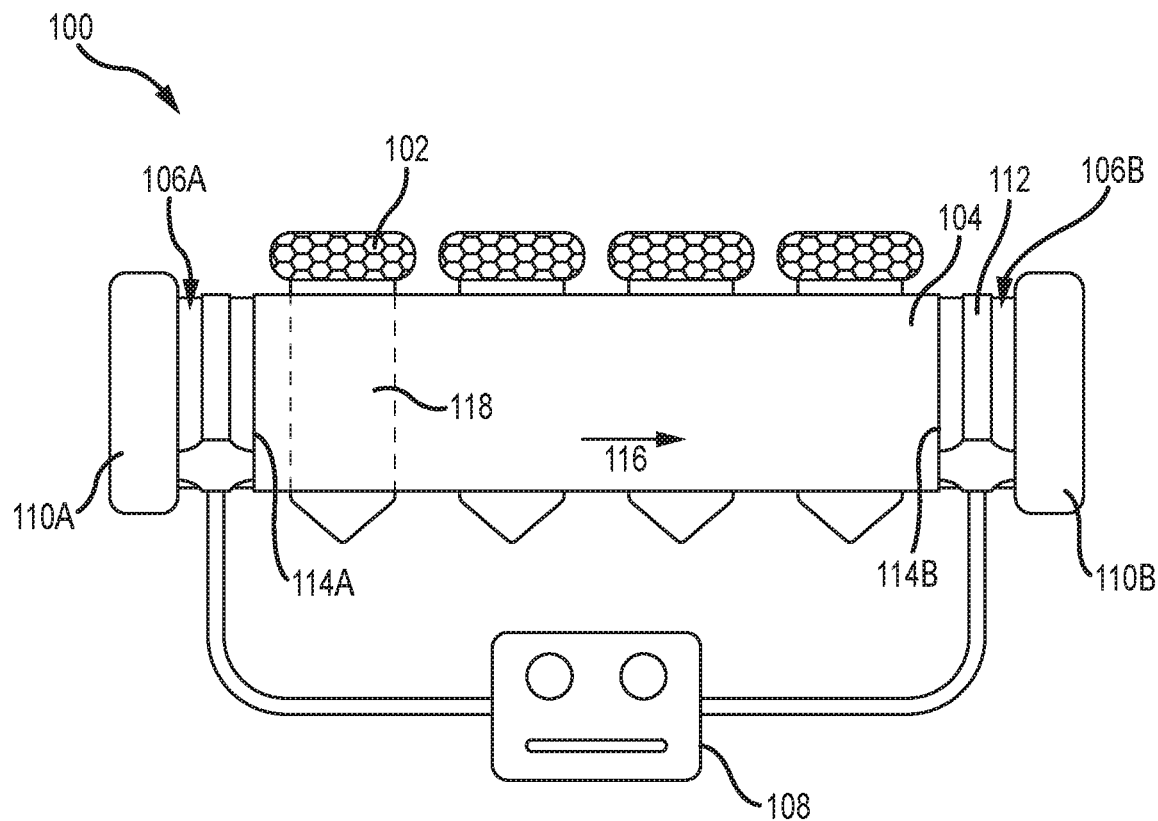
FIG. 1 shows an external ultrasonic agitator system in accordance with embodiments of the present disclosure.

The present disclosure may be understood by reference to the following detailed description, taken in conjunction with the drawings as described below. It is noted that, for purposes of illustrative clarity, certain elements in various drawings may not be drawn to scale.

Adipose tissue is an abundant, accessible, and replenishable source of adult stem cells that can be isolated from liposuction aspirate and waste tissue. A conventional method of isolating stem cells relies on a complicated ex vivo treatment with collagenase and exogenous digestive enzymes.

The present disclosure provides electromechanical devices and methods for harvesting the pluripotential cells from fat tissue, which is a readily available adult tissue source. The electromechanical device described herein includes an electromechanical agitator designed to disrupt and homogenize harvested fat tissue and to extract the stromovascular component from the fat tissue. The present disclosure also provides a centrifuge for concentrating the separated stem cells. The centrifuge is operated in a temporal sequence with the electromechanical device.

In some embodiments, the electromechanical devices may include an external ultrasonic agitator that includes a resonant horn to accommodate specimen containers. The present disclosure also provides a specimen tube that includes ridges or grooves for acoustic impedance matching between the horn and the fat tissue.

The ultrasonic energy in the external ultrasonic agitator system creates ultrasonic cavitation in the fat tissue, which accomplishes dispersing, de-agglomerating, disrupting and disintegrating of adipose cells prior to the centrifugal step. The external ultrasonic agitator system utilizes intense ultrasonic cavitation and mechanical forces to separate stem cells and stromal vascular fraction from white adipose tissue or fat cells. Since strong cavitation may lyse fat cells and red blood cells, the resulting hematopoietic stem cells, plasma platelets and other health factors of lipo-aspirate are retained in the final product. The ultrasonic procedure can avoid unnecessary laboratory and chemical or biological manipulations. The ultrasonic procedure is simple, straightforward, and sterile and provides isolation of stem cells from fat produced in accordance with FDA 361 and Good Manufacture Practice guidelines. This ultrasonic procedure is very fast and thus allows extracted stem cells to be used off-label and at the discretion of attending physicians. Since the mesenchymal stem cells and stromal vascular fraction are extracted from the patient, it is also autologous with minimal risk of an immune response, showing potential for directed clinical therapy against a variety of disease and damaged tissue.

The required energy density can be achieved through integration of the specimen vials or tubes directly into the mechanically fine-tuned ultrasonic horn. For a high intensity ultrasound generator, a resonant horn is an element that transfers mechanical energy from the oscillating piezoelectric transducers to a work piece, such as specimen tubes or vials. For example, each of two or four polyvinyl caped vials may contain adipose tissue fluid removed from abdominal lipo-suction procedure. Liposuction source may include other parts of the body besides the abdomen.

In some embodiments, the electromechanical devices may include an agitator probe that can contact the fat tissue inside the specimen container. The agitator probe may cause rotatory or vibrationary agitation inside the specimen container. The devices may include an agitator cap removably coupled to seal the specimen container for agitating the sample. The devices may also include an aspiration cap which can replace the agitator cap for centrifuging the agitated sample. The present disclosure also provides a specimen tube that includes ridges or grooves for improving efficiency of the agitation.

The present disclosure also provides a sterile method for harvesting fat tissue from a patient and extracting stem cells from the fat tissue and reintroducing into the patient in 15-30 minutes. The sterile method uses an intense ultrasonic excitation, or rotatory or vibratory agitation, followed by a differential centrifugation, which is a simpler, more effective, minimally invasive and sterile procedure for more efficient recovery of adipose somatic stem cells and stromal vascular fraction than conventional techniques.

The following section describes the design features and functionality of an external ultrasonic agitator device that can adjust ultrasonic frequency and amplitude for optimal settings useful for clinical application as described herein. The electromechanical device described herein combined with the described process can greatly simplify the availability of mesenchymal stem cells derived from fat in real time the clinical setting. Preservation of sterility, minimizing use of external agents, and instrumentation that can be used by any hospital personnel are important practical features. The extraction process of stem cells from a fat sample may be completed in about 15-30 minutes. The present disclosure provides clinical investigators with an effective tool for rapidly extracting pluripotential cell pellet from harvested fat sample that is often discarded. The device can greatly improve the efficiency of extraction and is user friendly for such applications. A method for cellular anatomical localization of the derived product is described.

An external ultrasonic field may be applied to a sealed fat containing tube. The electromechanical vibratory agitator provides ultrasonic power amplification by resonance. The electromechanical vibratory agitator includes a horn for amplifying the ultrasonic power. The agitator provides amplified ultrasonic power that is used for the break-down of fat samples.

For a conventional ultrasonic activation of vials in an ultrasonic cleaning tank, the water surrounding the vials takes most of the energy. The power in a 50 mL vial is less than 0.1 watt for ultrasonic cleaning. For ultrasonic cell separation processes, such a low power level is ineffective. Thus, a power boost for ultrasonic energy is used for stem cell isolation and recovery. The power boost may exceed 500 times.

FIG. 1 shows an external ultrasonic agitator system in accordance with embodiments of the present disclosure. External ultrasonic agitator system 100 includes two transducers 106A-B firmly attached to a resonant horn 104 that may be light and rigid. Each of transducers 106A-B may be formed of multilayer piezoelectric crystals 112. The resonant horn 104 can accommodate aseptic tissue containers 102 and can also amplify and transfer ultrasonic energy from the transducers 106A-B to the aseptic tissue containers 102. The horn 104 may include dual opposing ends 114A-114B. Each of ends 114A-114B is connected to one side of the respective transducer 106A or 106B. The horn 104 has a length of multiples of ½ wavelength.

The horn 104 includes an elongated body extending along a longitudinal axis 116 between two opposed ends. The horn includes elongated holes 118 that are transverse to the longitudinal axis. The resonant horn 104 can accommodate four tissue containers or specimen tubes 102 in this example. In other embodiments, the horn may include more or fewer holes 118 to accommodate more or fewer tubes 102. The resonant horn 104 may be formed of a light weight metal, such as titanium or aluminum.

The external ultrasonic agitator system 100 may also include an outer backing end 110A-B on each outer side of the respective transducers 106A-B. Each of the outer backing ends 110A-B is configured to transmit the ultrasonic vibration only toward the horn 104.

The external ultrasonic agitator system 100 may also include a power generator module or wave generator 108 that drives the piezoelectric transducers 106A-B. For example, the power generator module 108 may be a phase shifted square wave generator which is electrically coupled to the piezoelectric drivers. The phase shifted wave generator 108 can be controlled to generate two phase-shifted waves. The wave generator 108 may produce a standing wave in the horn 104. The wavelength may be about 20 cm at 25 kHz in the horn 104 that has a sound velocity of about 5000 m/s.

The wave generator 108 can also be self-tuned to the tissue tube or container including specimen. In a particular embodiment, the external ultrasonic agitator system 100 may include a self-tuning circuit that is based on a power current plateau. The system 100 may also include a self-tuning circuit with an acceleration sensor to boost optimal resonance.

The tissue containers or specimen tubes 102 are positioned at the locations in the horn for maximum ultrasonic power. Generally, the number of tubes in the resonant horn may be an even number, for example, at least 2, 4, 6, among others, such that the centrifuge head is counterbalanced with the even number of tubes that have filled specimen, such as fat tissue.

The frequency in the system 100 may be tuned to break apart the larger collagen stroma and yet preserve the viability of the smaller stromovascular cells.

The vibratory energy or amplitude in the system 100 may also be modulated by a heat measuring servo mechanism, which is implemented into the power generator module or wave generator. The system 100 may include a temperature sensor (not shown) for measuring the temperature of the horn 104 near the specimen tubes 102. The sensor can measure specimen temperature in the specimen container during ultrasonic disruption. The temperature sensor can provide feedback for the system 100 to adjust the output of the wave generator 108 to prevent the tissue specimen from overheating. For example, if the temperature exceeds 43.5° C., the vibratory amplitude will be reduced, because the excess ultrasound energy may damage the viability of the cells.

The system 100 may include a self-tuning capability and subject the sealed specimen tubes to high fluxes of ultrasonic dispersion/separation energies. The system 100 may include an acceleration sensor coupled to the horn to provide feedback for self-tuning and optimum power output.

Figure 2:
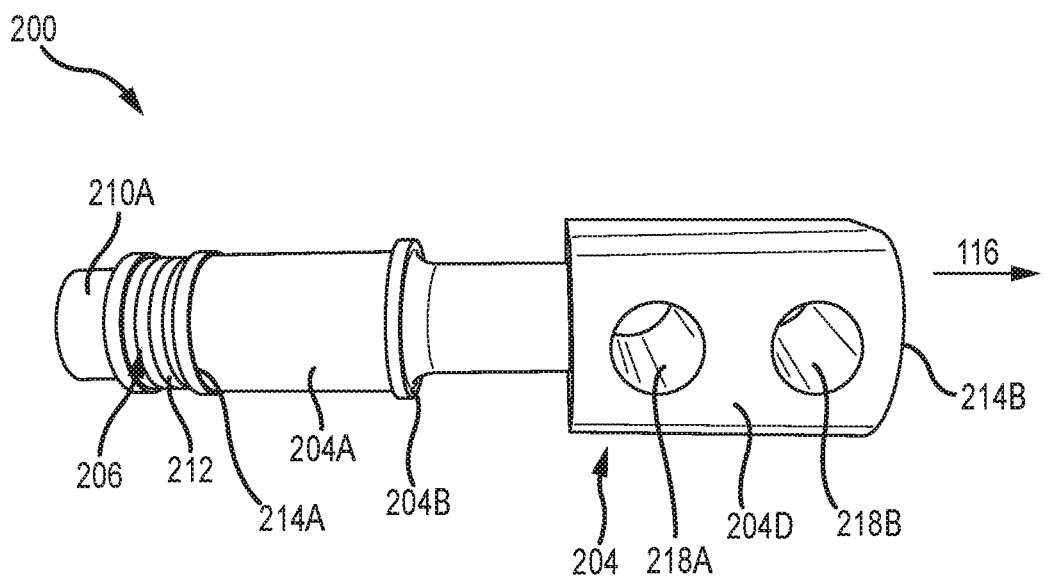
FIG. 2 shows a prototype of a resonant horn in accordance with embodiments of the present disclosure.

In an alternative embodiment, one transducer may be attached to an end of the horn to form a standing wave in the horn. One opposing end of the horn is configured to reflect the ultrasonic wave generated by the transducer. FIG. 2 shows a prototype of a resonant horn in accordance with embodiments of the present disclosure. As show, one transducer 206 including four piezoelectric crystals 212 is attached to only one end of the horn 204. Also, the horn 204 accommodate two specimen tubes (not shown). The ultrasonic wave generated by the transducer 206 is reflected from an opposing end with a phase difference of about 180° C. from the incoming wave generated from the transducer 206. The reflected wave and the wave generated from the transducer 206 forms a standing wave.

The horn 204 may include a first portion 204A attached to one of the crystal disks 212 to the left side of the horn 204. The first portion 204A has a diameter close to the crystal disks 212 that transmit ultrasonic waves along a longitudinal axis 116. The horn 204 also includes a second portion 204C which has a smaller diameter than the first portion. The horn 204 also includes a transition portion 204B between the first portion 204A and the second portion 204C. The transition portion 204B has a larger diameter than that of the first portion 204A and is smoothly transitioned from the second portion 204C. The horn 204 also includes a third portion 204D coupled to the second portion 204C. The third portion 204D has a larger diameter than the crystal discs 212 and includes two through-holes 218A-B that are spaced apart along the longitudinal axis 116 and accommodate two specimen tubes, respectively.

It will be appreciated by those skilled in the art that the number of crystal disks in the transducer may vary. The higher number of crystal disks may generate high ultrasonic energy. The crystal disk thickness may vary to provide desired ultrasonic frequency.

The piezoelectric transducer 206 may be firmly attached to one end of the horn and may be driven by a square wave power generator module 108. The ultrasonic wave may travel in the horn at a velocity of 5000 m/second and with a wavelength of 20 cm for a frequency of 25 kHz. In this example, the horn 204 can accommodate two specimen tubes. The length of the horn is a half-wavelength multiplier. The phase shifted wave generator 108 can be adjusted to form an ultrasonic resonator in the horn 204.

The ultrasonic transducer 206 may include PZT5 piezoelectric crystal discs that are clamped together by a strong bolt to form a serial mechanical oscillator, which has vibration amplitudes from each crystal disc reinforced in synchronization. The crystal discs 212 are electrically connected in parallel and are driven by high voltage pulse wave signals. The driving voltage wave signals may be maintained at a mechanical resonance frequency of the piezoelectric crystals 212.

Figure 3:
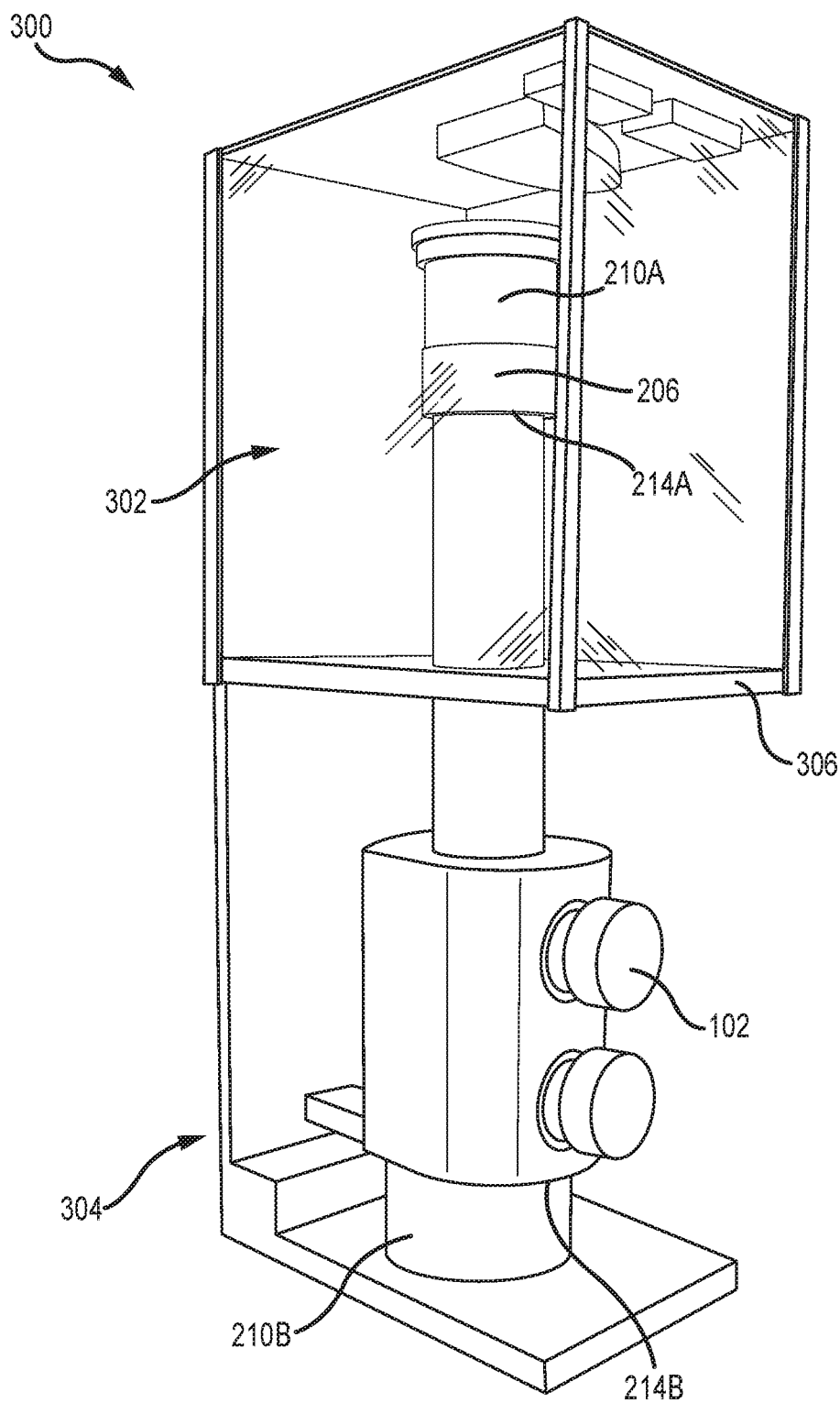
FIG. 3 shows a countertop ultrasonic agitator device that includes the horn of FIG. 2.

FIG. 3 shows a countertop ultrasonic agitator device 300 that includes the horn 204 of FIG. 2. The countertop ultrasonic agitator device 300 has an upper portion 302 that includes an ultrasonic transducer 206 consisting of piezoelectric crystal disks 212. One of the crystal discs 212 is connected to a resonant horn 204, which amplifies the mechanical displacement of the ultrasonic oscillation from the crystal discs 212.

The horn 204 may be constructed of a strong and lightweight metal alloy, such as titanium alloy or aluminum alloy, to transfer mechanical vibration from transducers to the specimen tube. The length of the horn 204 between two opposing ends 214A-B may be configured in relation to the wavelength of the traveling ultrasonic wave. For example, the length may be a multiple of the half wavelength traveling in the horn 204.

The countertop ultrasonic agitator device 300 also has a lower portion 304 that includes the resonant horn 204 to accommodate two specimen tubes 102. At the bottom end 214B of the horn 204, the countertop ultrasonic agitator device 300 includes a backing 210B that reflects the ultrasonic wave generated by the transducer 206. The backing 210B is configured to provide the wave reflection in roughly 180° for the ultrasonic wave generated from the transducer 206 above a top end 214A of the horn 204 and transmitted through the horn 204 toward the backing 210B at the bottom of the device 300. The reflected wave from the backing 210B forms a standing ultrasonic wave with the ultrasonic wave generated by the transducer 206. Another backing 210A attached to the transducer 206 is configured to have the transducer vibrate only toward the horn.

The countertop ultrasonic agitator device 300 may also include a separation plate 306 that separates the upper portion 302 from the lower portion 304. The transition portion of the horn 204 sits on top of the separation plate 306.

Two specimen vials are placed in locations where the local mechanical vibrations and cavitation action are maximized. The oscillation frequency may vary with the dimension and material of the piezoelectric transducer. The amplitude of the ultrasonic transducer can be adjusted by varying the power of the ultrasonic generator in order to vary the mechanical amplitude of vibration or ultrasonic energy into the specimen tube.

Specimen Tube

The tissue container 102 may be a specimen tube with inner wall fins/grooves for improved ultrasonic coupling of the fat tissue with external energy sources. The shape and walls of the tissue container can be optimized for maximum transfer of externally applied ultrasonic dispersive energy. For example, the container may include internal wall projections into the specimen containing lumen for impedance matching between the horn and the fat tissue.

Figure 4A:
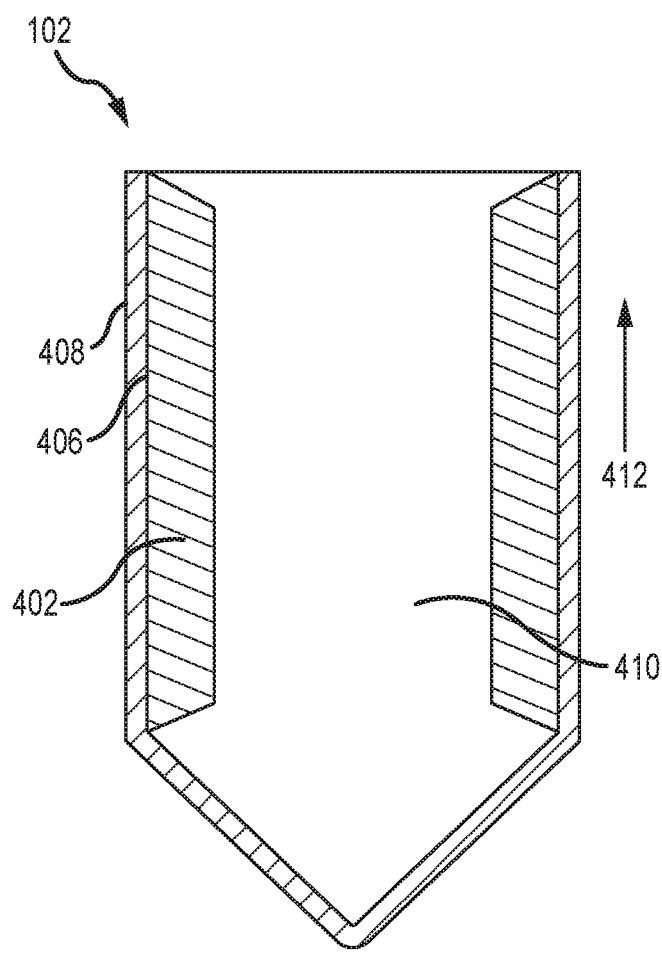
FIG. 4A is a side sectional view of a specimen container including a plurality of ridges on an inner wall in accordance with embodiments of the present disclosure.
Figure 4B:
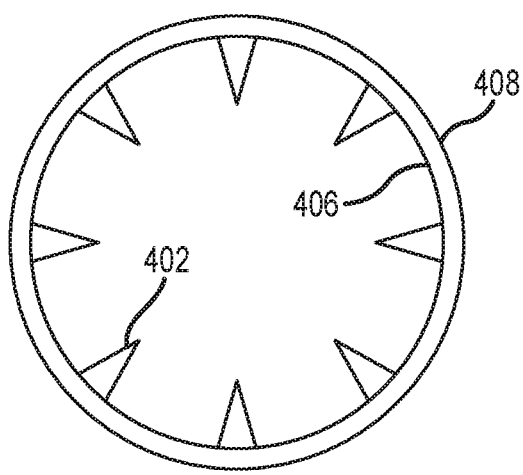
FIG. 4B is a top view of the specimen container of FIG. 4A.
Figure 4C:
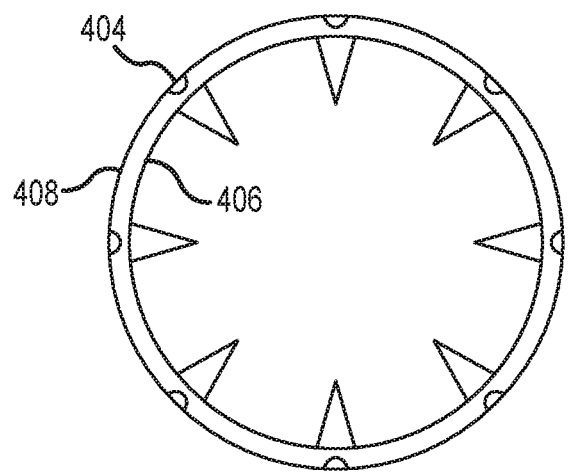
FIG. 4C is a top view of an alternative design of the specimen container including grooves and ridges in accordance with embodiments of the present disclosure.

FIG. 4A is a side sectional view of a specimen container including a plurality of ridges on the inner wall in accordance with embodiments of the present disclosure. FIG. 4B is a top view of the specimen container of FIG. 4A. FIG. 4C is a top view of an alternative design of the specimen container including grooves and ridges in accordance with embodiments of the present disclosure.

As shown in FIGS. 4A-4C, the internal ridges or fins 402 are radially inwardly projected from the wall 406 of the tube 102 and are oriented along the longitudinal axis 412 of the tube 102. The outer grooves 404 open radially outwardly from the outer wall 408 of the tube 102 and are oriented along the longitudinal axis 408 of the tube 102. These ridges 402 or grooves 404 help provide acoustic coupling between the horn and the fat tissue inside the lumen 410 of the tube 102 for optimal ultrasonic energy transfer.

The geometry of the ridges, fins, and/or grooves may be tuned for optimal energy coupling between the horn and the semi-liquid contents inside the tube. In a particular embodiment, the specimen tube 102 may include a specially designed conical end, like the ones used in larger centrifuges. It will be appreciated by those skilled in the art that the shape of the specimen tube may vary. The configuration of fins or grooves of the specimen tube may also vary, such as shapes of the fins or grooves, spacing between the fins or grooves or arrangement of the fins or grooves.

These tubes 102 are also configured to have minimal sound reflection which may lead to destructive cavitation effects and cellular damage to the stromovascular component.

These specimen tubes 102 may be constructed from plastic, such as polyethylene, or any material that is not brittle, but is sufficiently rigid, and is also semitransparent for the fat sample in the tube to be visible. These specially designed specimen tubes 102 are sterile and may be supplied to the surgeon for harvesting fat tissue in the medical care room or unit, such as an operating room, a medical doctor office, or an emergency room among others. The specimen tubes with ridges and/or grooves 102 may be injection molded.

As an example, a sample vial may be a 50 mL conical centrifuge tube with an aspiration cap of 30 mm diameter. The vial may be about 115 mm long and have a conical bottom tip. The sample vial is autoclavable and freezable.

Electromechanical Agitator Device with Agitator Cap and Aspiration Cap

In an alternative embodiment, the electromechanical agitator device may include a rotary agitator probe, or a vibratory or linear piezoelectric specimen agitator to provide sufficient energy to create cavitation in tissue in the tube. The rotatory agitator probe may be inserted into the tube and may be in direct contact with the fat.

The tube may be a conventional tube without any ridges, fins, or grooves. Alternatively, the tube may be specially designed to include ridges, fins and/or grooves for improved efficiency, as disclosed in related texts with respect to FIGS. 4A-4C. The tube may also be modified by including a number of metal rods that act like the ridges or fins, as disclosed in detail with respect to FIG. 7 later.

In some embodiments, the rotatory agitator probe may be driven by an ultrasonic or subsonic rotary electromechanical engine (e.g. electric motor) for breakdown of collagen/fibrous structure to accomplish tissue dispersion to separate stromovascular cells. In alternative embodiment, the linear piezoelectric specimen agitator may include a vibratory electromechanical engine for the breakdown of collagen/fibrous structure. The agitator probe may include rotary or oscillating engines that are used for surgical bone drilling or cutting instrumentation. Examples of such readily available electromechanical engines are the STRYKER@ microdrill, STRYKER@ impaction drill, Medtronic Xomed XPS power set, Medtronic Triton system and variety of similar power electromechanical engines readily available in most existing operating room suites.

Figure 5:
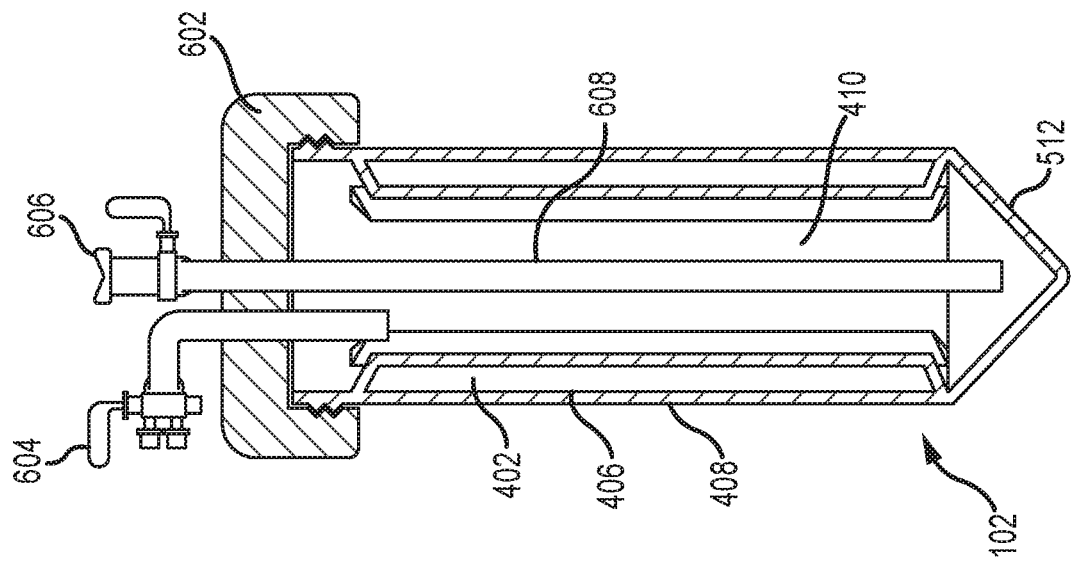
FIG. 5 illustrates an example electromechanical rotatory agitator device including a tissue container and an agitator cap coupled to an agitator probe in accordance with embodiments of the present disclosure.

FIG. 5 illustrates an example electromechanical rotatory agitator device including a tissue container and an agitator cap coupled to an agitator probe in accordance with embodiments of the present disclosure. The electromechanical rotatory agitator device 500 includes a tissue container or specimen tube 102 removably coupled to a sealed agitator cap 502. The tube 102 includes an open end 514. The agitation cap 502 is sealed to the open end of the tube. With the agitator cap, the specimen tube can be sealed for tissue agitation, tissue dispersion, tissue emulsion, or tissue shearing.

The electromechanical rotatory agitator device 500 also includes an agitator probe having a number of rotors 510 attached to a rotary shaft 508, which is coupled to the agitator cap 502. The agitator cap 502 may include a central hole configured to allow the rotatory shaft 508 to extend inside the lumen 410 of the tube 102.

The electromechanical rotatory agitator device 500 also includes a sealed sleeve bearing 506 coupled between the rotary shaft 508 and the agitator cap 502 to allow the rotary shaft to freely rotate and also to seal the central hole of the agitator cap 502. The sleeve bearing 506 may be in a tube form or ring form. The sleeve bearing 506 may have an inner diameter larger than the outer diameter of the rotary shaft 508. The sealed sleeve bearing 506 may be formed of a plastic with low friction, such as polytetrafluoroethylene (PTFE). The sealed bearing 506 is embedded in the agitator cap 502.

On two opposite sides of the agitator cap 502, one stopper 504B is coupled to the rotatory shaft 508 inside the lumen 410 of the tube 102 and another stopper 504A is coupled to the rotary shaft 508 outside the tube 102. The two stoppers 504A-B are configured to prevent the rotatory shaft 508 from movement along the longitudinal axis 412. The rotatory shaft 508 can be removed such that the sleeve bearings 506 can be thoroughly cleaned.

In some embodiment, a stabilizer may be added at the end of the rotatory shaft outside the agitator cap to further stabilize the rotation of the rotor if necessary.

The ridges or fins on the inner wall (as shown in FIG. 5) or the grooves on the outer wall of the tube (similar to that shown in FIG. 4C) may provide improved efficiency of rotary blender function. The geometry of the ridges, fins and/or grooves may be tuned for optimal energy coupling between the horn and the semi-liquid contents inside the tubes. In some embodiments, fins may be used inside the tube. In some embodiments, grooves may be used outside the tube. In some embodiments, a combination of fins and grooves may be used in the tube.

In a particular embodiment, the specimen tubes may include a specially designed conical end 512, like the ones used in larger centrifuges. It will be appreciated by those skilled in the art that the shape or configuration of the specimen tube may vary.

Figure 6:
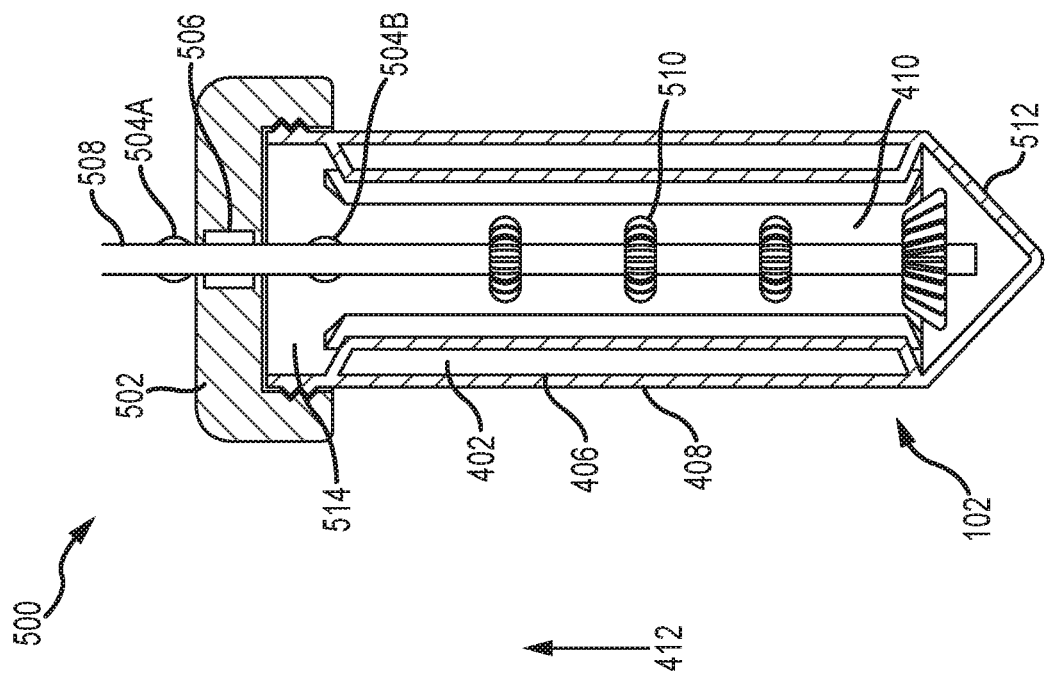
FIG. 6 illustrates the tissue container of FIG. 5 and an aspiration cap coupled to a syringe drawing port to replace the agitator cap of FIG. 5 in accordance with embodiments of the present disclosure.

FIG. 6 illustrates the tissue container of FIG. 5 and an aspiration cap coupled to a syringe drawing port to replace the agitator cap of FIG. 5 in accordance with embodiments of the present disclosure. The tube 102 with the aspiration cap 602 can be placed in a centrifuge system to complete the separation phase. The aspiration cap 602 is coupled to a syringe drawing port 606 connected to a center cannula 608, which is used to aseptically aspirate the concentrated stromovascular cellular content at the bottom 512 of the tube 102 at the completion of the centrifuge stage described herein.

The aspiration cap 602 is also coupled to an air inlet 604, which allows air to flow inside the tube. The air inlet 604 keeps the lumen 410 of the tube 102 at an atmospheric pressure after the extraction of the stem cells from the bottom 512 of the tube 102 through the syringe drawing port 602 and the center cannula 608, such that specimen extraction can be performed without generating undue negative pressure within the specimen container.

The specimen tube 102 of FIGS. 4A-4C, with the aspiration cap 602 as shown in FIG. 6, can be used in the system 100. Throughout the ultrasonic dispersion process in system 100, the tube 100 is sealed with the aspiration cap 602 such that the fat tissue inside the specimen tube remains sterile.

Figure 7:
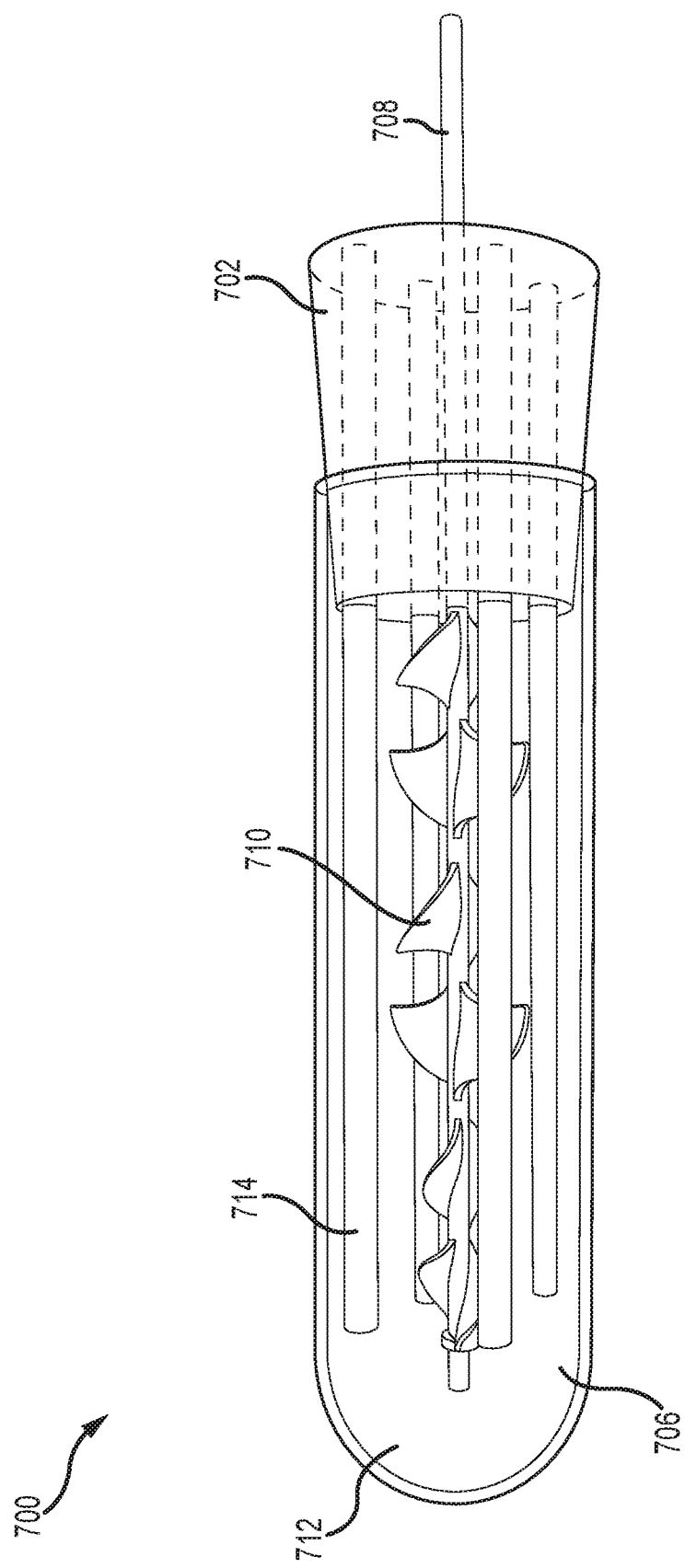
FIG. 7 illustrates a conventional tube with an agitator cap in accordance with embodiments of the present disclosure.

FIG. 7 illustrates an electromechanical rotary agitator device including a conventional tube with an agitator cap in accordance with an embodiment of the present disclosure. The conventional tube 706 does not include any ridges or fins as shown in FIGS. 4A-C, FIG. 5 or FIG. 6. As shown in FIG. 7, the agitator device 700 includes a specimen tube having a closed bottom and an open end sealed with an agitator cap 702. The agitator device 700 also includes rotors 710 coupled to a stator 708 that is driven by an electric motor (not shown). The rotors 710 agitate the fat tissue inside the tube 706.

The agitator cap 702 includes a central through-hole through which a stator rod 708 extends into the specimen tube. The stator rod 708 includes an outer end extending outside the agitator cap 702. The stator rod 708 also includes an inner end that extends through the central through-hole of the agitator cap 702 toward the bottom 712 of the tube 706, but does not contact the bottom of the tube. The outer end of the stator rod can be coupled to an electric motor to cause the rotation of the rotors.

Inside the tube, a plurality of rotors 710 are coupled to the stator rod 708 and are spaced apart from each other. The rotors 710 are driven to rotate by the electric motor coupled to the outer end of the stator rod 708. It will be appreciated by those skilled in the art that the rotors may vary in shapes and the number of rotors to accomplish optimal break-down of the fat tissue in the tube.

In the conventional tube, a few stabilizing metal rods or bars 714 may be added to act like the ridges or fins inside the tube to help improve the efficiency of the mechanical agitation of the fat tissue. The metal rods 714 have one end coupled to the agitator cap 702 and one end extending toward the bottom 712 of the tube 706, but does not contact the bottom. The stabilizing bars also provide counter spin stabilization of specimen within the specimen container.

Because of the sample in the sealed tube 706 or container remains sterile, the aspiration of the concentrated stromovascular cellular content is performed by using a syringe and a lock system to maintain content sterility. The tube 706 includes the agitator cap 702 coupled to the stator rod 708 to which the rotors 710 are attached. Thus, this method does not require introduction of any new molecules into the processing of fat tissue and eliminates the possibility of viral or bacterial contamination of the specimen. The specimen reintroduced to the patient is genetically autologous, contains only the original tissue components, and thus obviates possibility of transmissible organisms.

The agitation for tissue dispersion and isolation can be performed by a health provider in existing and certified operating room facilities, such as an operating room, an emergency room, or a medical office or a medical care room or unit. After the agitation, the tube is handed off the field and given to the support staff for the centrifuge.

Example Ultrasonic Resonant Agitator System

An example ultrasonic horn may be about 380 mm long, 108 mm wide, and 165 mm in height with a side loading. The example resonant horn may hold two 50 mL caped vials.

An example wave generator or power unit may be about 280 mm long, 203 mm wide, and 159 mm in height. The wave generator uses AC power, for example, 110 V AC×5 A×60 Hz (Circuit breaker rating). The transducer may have a frequency of 25.09 KHz+/−50 Hz.

The transducer may include four crystal discs that may be formed of PZT5 piezoelectric crystals. Each disc may have a diameter of 50 mm and a thickness of 6.5 mm. The four crystal discs may be pre-stressed via a center compression bolt. The ultrasonic resonant agitator system may have a maximum capacity of 500 W.

The power unit may include a power on/off switch and has a Sonic Activation Duty Cycle ranging from 10% to 100% (10% to continuous). The power unit may also include a Sonic Activation ON/OFF switch. The sonic energy can be adjusted by a dial setting. The electrical wave amplitude (sonic energy) can be adjusted. The power unit may also include a Frequency Fine Tuning.

The ultrasonic resonant agitator system may adjust its temperature. The ultrasonic resonant agitator system may include a safety circuit in real-time by using a temperature sensor (e.g. an IR sensor or thermocouple) for temperature measurement that provides feedback to the system to control the duty cycle of the wave generator or power unit. The temperature sensors, such as thermocouples, may use an isolated battery power source.

The ultrasonic resonant agitator system may also include a display. For example, the power unit may include a front panel that displays a green light indicating AC Power "ON" light. The power unit may also include a Sonic Activation Status indicator light yellow and indicate Ultrasound "ON." The power unit may also include a red light for indicating a specimen tube or vial being overheated. The power unit may also include rear panel input/output connections and an exhaust fan.

The ultrasonic resonant agitator system may include a display of vial temperatures. For example, an LCD digital display may show temperatures of vials or a temperature limit setting at an accuracy of 0.1° C.

The operating procedure may include the following steps: (1) keep the power unit power on/off switch in an "OFF" position; (2) connect interface and sonic power cables between the power unit and ultrasonic horn; (3) preset the power unit controls including turning Sonic Energy & DC Bias Adjust to minimum, turning ultrasound toggle switch to an "OFF" position, selecting desired duty cycle, setting Frequency Fine Tuning knob to a mid-position, and inserting two sample vials containing liquid specimen.

For testing, the power unit is turned to an "ON" position to observe the following normal displays and indications: green power-on light is on; ultrasound status light is off; and the ultrasonic horn displays correct vial temperature readings after a brief thermocouple sensor start-up period to have up to 2° C. accuracy.

The next step is to adjust the desired temperature limit for the resonant horn by depressing the toggle switch and turning the limit adjustment knob simultaneously and to release the toggle switch and lock adjustment knob after the desired limit is obtained. Note that when the vial temperature exceeds the limit, sonic energy is momentarily interrupted until vial temperature drops below set limit, such as 2° C. below. The Sonic Activation Status indicator light on power unit will turn red during this period.

The operating procedure may include:

(1) Turn Sonic Energy & DC Bias Adjust knob clockwise for a meter reading of approximately 250 VDC (dial setting of 5);

(2) Turn ultrasound ON/OFF toggle to "ON" position. The sonic energy and sonic Activation Status indicator light (yellow) turns on within 10 seconds;

(3) During the period when sonic energy and yellow light is on, adjust the Frequency Fine Tuning knob (clockwise initially) for a maximum dip (approximately 50V) in DC Bias Voltage, indicating resonant oscillation of the horn. For out-of-tune frequencies, there is little or no dip in DC Bias Voltage, indicating little or no horn oscillations. Further fine-tuning can be obtained by observing the frequency of stray electrical signals picked up by a nearby oscilloscope. Note that the liquid specimen property and filling level in vial may affect the frequency setting slightly;

(4) Reduce or re-adjust Sonic Energy & DC Bias Adjust knob for the desired sonic energy;

(5) Re-select the desired duty cycle other than the 1.0 "continuous" initially selected. The duty cycle is based on a 10-seconds ON/OFF clock period. The new duty cycle selected may take effect in a maximum delay of 10-seconds;

(6) Note that there is a built-in overheat safeguard for internal power driver devices. Sonic energy is interrupted until overheating condition is off. Such overheating occurs when the DC Bias Voltage setting is too high, electrical waveform becomes erratic, and the piezoelectric crystals cease to function properly;

(7) An isolation transformer inside the Power Unit amplifies the AC power delivered to the power stage. The 25 KHz square-wave high voltage electrical signals are delivered to the piezoelectric crystals, which are electrically isolated from the titanium horn. Note that for further safety precaution, skin contact with the horn during operation should be avoided; and (8) Adjusting the Frequency Fine Tuning knob may encounter the first-harmonic resonance oscillation of the device (around 28 KHz). Oscillation intensity would be much lower at higher frequency. The Frequency Fine Tuning may adjust frequency from 22.4 kHz to 29 kHz in a small increment by adjusting dial count, as shown in Table 1.

| DIAL COUNT | Frequency (kHz) |
| --- | --- |
| 000 | 29 |
| 100 | 28 |
| 200 | 27.3 |
| 300 | 26.2 |
| 400 | 25.6 |
| 500 | 25 |
| 600 | 24.5 |
| 700 | 24 |
| 800 | 23.2 |
| 900 | 22.7 |
| 999 | 22.4 |

Ultrasonic Agitation Process and Applications of Extracted Stem Cells from Fat Tissue The present disclosure provides devices and methods that can help clinicians rapidly extract stromovascular cells from harvested fat tissue of a patient, process the fat tissue rapidly, and preserve the sterility of the extracted stromovascular cells. The procedure does not require any particular laboratory skills, and the procedure does not introduce foreign substances which could pose safety issues when reintroduced back into the patient.

Also, sterility is preserved throughout all the steps. Additionally, the processing of the fat sample can be performed by medical personnel without any laboratory or extensive device training. For these and other reasons the present device and system possesses compelling advantages over existing or conventional technologies for concentration of stromaovascular cellular layer. The present device is better, faster, and cheaper than the conventional technologies for cellular concentration.

The present disclosure provides an aseptic technique of concentrating stromovascular cells within human fat specimen and a system for autologous re-implantation into the same patient within a period of 15-30 minutes without the specimen leaving the operating room site.

The ultrasonic agitation process or dispersion process by using the external ultrasonic agitator system 100 or system 300 may take about a period of 5-10 minutes at energy levels that may be optimized. After the ultrasonic dispersion process, the tube is moved from the electromechanical agitator to an adjacent centrifuge and is subjected to gravitational separation for a period of about 4 to 8 minutes. After completion of both the vibratory cycle and the centrifugation cycle, the desired stem cells are aseptically aspirated. A sterile syringe may be used to aspirate the desired contents from the apex of the tube. The desired cellular contents can be drawn into the sterile syringe and can be used by a clinical personnel. The cellular contents or stromovascular cells contain an enhanced number of pleuro-potential cells derived from the processed fatty tissue. Because the fat tissue has been mechanically stressed by the ultrasonic agitation, many of the larger cells may release various growth factors and chemo tactic peptides that further enhance the responsiveness of the viable pleuro-potential cells that are concentrated and reintroduced into the same patient in any desired anatomical location.

A health provider can therefore readily and aseptically obtain 3 to 5 mL of concentrated stromovascular cells harvested from a sealed tissue tube or container of approximate 50 mL. About 2 to 3 mL of desired cellular contents may be produced. For an ultrasonic resonant agitator system that can accommodate 2 or 4 tubes, a single processing cycle may yield 5 to 10 mL of desired cellular contents or stromovascular cells.

Similarly, the agitation process by the agitator probe with an agitation cap as shown in FIG. 5, followed by the centrifuging step by the probe with the aspiration cap as shown in FIG. 6, may take about less than 30 minutes, preferably 15 minutes or 10 minutes. The ultrasonic dispersion process or agitation process eliminates the need for introducing reagent (e.g. collagenase or other enzymatic digestion) into the living specimen, such as fat tissue.

Figure 8:
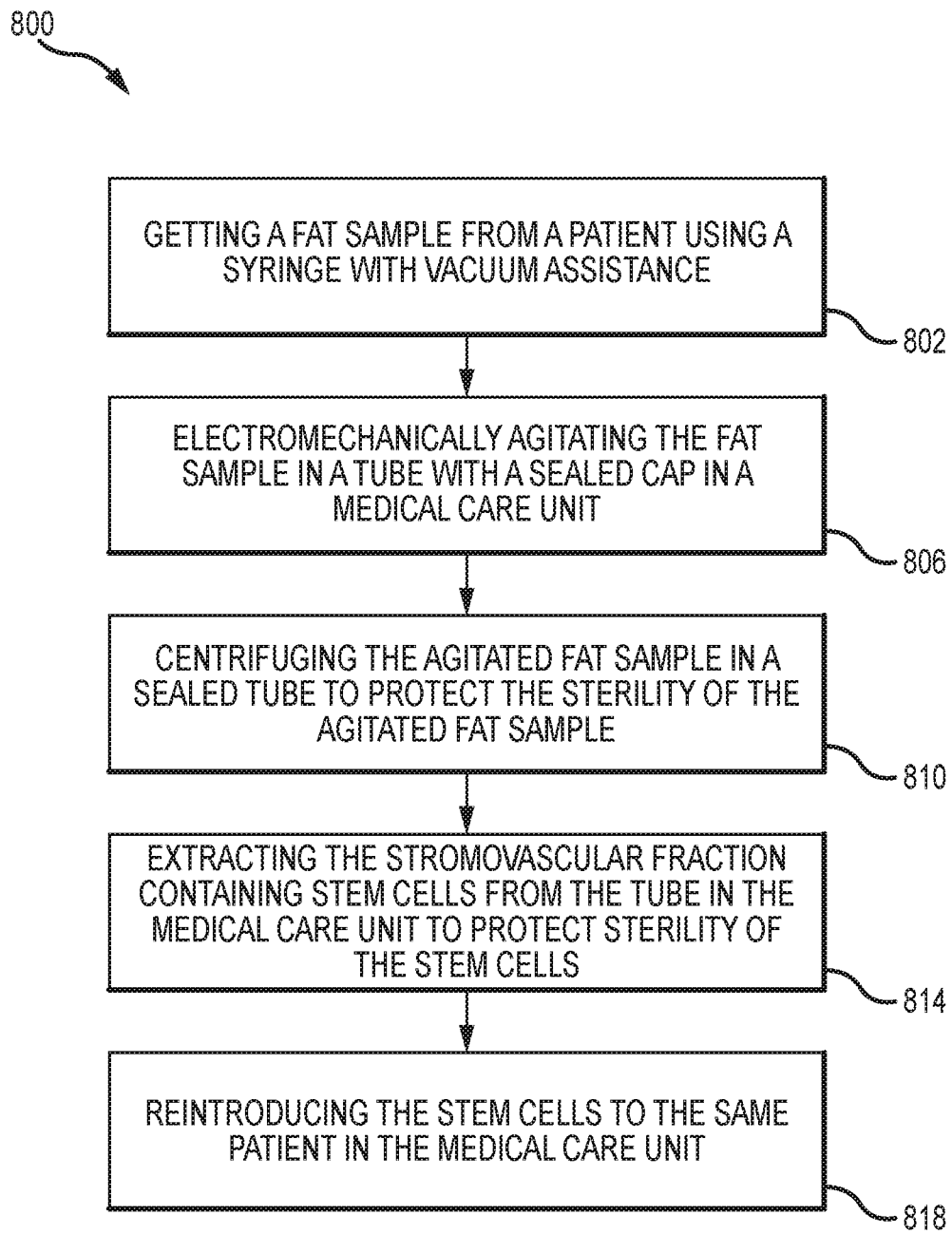
FIG. 8 is a flow chart that illustrates the steps of a medical procedure in accordance with embodiments of the present disclosure.

FIG. 8 is a flow chart that illustrates the steps of a medical procedure in accordance with embodiments of the present disclosure. Medical procedure 800 may include getting a fat sample from a patient using a syringe with vacuum assistance at step 802. Medical procedure 800 may also include electromechanically agitating the fat sample in a tube with a sealed cap in a medical care unit at step 806. An electric power source may be provided for agitating the fat sample. This agitating step may be accomplished by either the external ultrasonic resonant agitator 100 or 300 using the specimen tube as shown in FIGS. 4A-4C. The agitating may also use the rotatory agitator probe device as shown in FIGS. 5-7, or a linear vibratory probe (not shown). Medical procedure 800 may further include centrifuging the agitated fat sample in the sealed container to protect the sterility of the fat sample at step 810, followed by extracting the stromovascular fraction containing stem cells from the tube in the medical care room to protect sterility of the sample at step 810. The sealed container may be the same sealed container for the agitating step, centrifuging step and the extracting step, thus increasing the likelihood of maintain the sterility.

The medical procedure may also include reintroducing the stem cells to the same patient at step 818.

The process enables anatomical localization of the cellular graft, as opposed to current indiscriminate intravenous injection of cellular content with the hope that the stem cells will migrate to the desired site of clinical issue on their own and hypothetical guiding factors. The use of a cellular biological matrix with growth and chemotactic peptides is sterilely preserved.

In alternative embodiments, the present disclosure provides a biological retaining packet with cellular hydration port, which allows the use of the extracted stem cells for patients at a later time. Specifically, a regeneration matrix may be packaged in a specially designed pocket with a syringe connector port. The concentrated cellular contents obtained from the ultrasonic dispersion process and the centrifugation cycle can be injected into the specially designed pocket containing the Biodesign graft. The injection serves a dual purpose of hydrating the graft material and saturating the graft with enhanced cellular contents. The saturated graft can be used to repair tissue in any surgically desired area. The regeneration matrix with cellular contents offers enhanced tissue repair at specific anatomical area by virtue that the cellular content is anatomically localized and retained in the area of matrix insertion. In a particular embodiment, a sealed biological retaining packet containing acellular biological matrix with a cellular hydration port through which the harvested stem cells within the processed stromovascular fraction containing stem cells can be introduced for adhesion/hydration to the matrix for subsequent replantation.

The product is composed of high viability, mesenchymal stem cells and other important cell populations, including pre-adipocytes, endothelial cells, smooth muscle cells, fibroblasts, immune cells and a variety of growth factors. The product is more therapeutically efficacious than stem cells alone. It can be used for clinical regenerative healing in a variety of tissues in areas of cosmetic, periodontal medicine, orthopedics, osteoarthritis and other even more important treatments.

The electromechanical and ultrasonic resonator device can be used as alone or can also be used in combination with established enzymatic digestive process. The electromechanical and ultrasonic technologies described herein can function as process accelerators. A small amount of collagenase mixed with the specimen may accelerate the enzymatic breakdown of fat or other tissue when subjected to electromechanical energies by virtue of micro dispersion as well as direct energy induction of enzymatic digestion of collagen retaining matrix. Therefore, the present technology can be used in combination with the conventional technology to make the overall extraction significantly more efficient.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

The invention claimed is:

1. An apparatus for extracting stem cells from fat tissue, the apparatus comprising;
   a specimen container having a closed bottom and an open top;
   an electromechanical agitator inside the specimen container;
   an agitator cap removably coupled and sealed to the electromechanical agitator and configured to seal the open top of the specimen container to maintain specimen sterility; and
   an aspiration cap removably coupled and sealed to the open top of the specimen container to maintain specimen sterility, the aspiration cap including a syringe with a fluid channel for specimen extraction from the specimen container, wherein the aspiration cap and the agitator cap are configured to exchange or replace each other to couple to the open top of the specimen container.

2. The apparatus of claim 1, wherein the aspiration cap comprises an air inlet configured to keep the pressure inside the tube at an atmospheric pressure such that specimen extraction can be performed without generating undue negative pressure within the specimen container.

3. The apparatus of claim 1, wherein the electromechanical agitator comprises a stator rod and a plurality of rotors connected to the stator rod.

4. The apparatus of claim 3, wherein the edges of the plurality of rotors are round and smooth to minimize damage to stem cells.

5. The apparatus of claim 3, wherein the electromechanical agitator further comprises a plurality of lateral stabilizing bars to provide counter spin stabilization of specimen within the specimen container or the specimen container comprises a plurality of fins on inner wall of the container and/or grooves on outer walls of the container for improving efficiency of the electromechanical agitator.

6. The apparatus of claim 1, further comprising a sleeve bearing embedded within the sealed agitator cap configured to reduce friction.

7. The apparatus of claim 1, wherein the electromechanical agitator comprises a rotary or linear ultrasonic/subsonic driver to cause rotary or linear agitation.

8. A sealed biological retaining packet containing acellular biological matrix with a cellular hydration port through which the harvested stem cells according to claim 1 within the processed stromovascular fraction containing stem cells can be introduced for adhesion/hydration to the matrix for subsequent replantation.

9. A method for sterilely extracting stem cells from fat, the method comprising:
   placing a specimen container containing fat in an ultrasonic resonator;
   applying an external ultrasonic field to the fat to separate stem cells from the fat in a medical care room;
   placing the specimen container in a centrifuge to concentrate the separated stem cells;
   removing the specimen container from the centrifuge; and
   extracting the concentrated stem cells from the specimen container, wherein the specimen retains sterility through the sequence of the above steps, wherein the specimen container has an outer wall and a constant volume inside the outer wall.

10. The method of claim 9, wherein the specimen container comprises a plastic.

11. The method of claim 9, wherein the specimen container has a single lumen.

12. The method of claim 9, wherein a total time for sterilely extracting stem cells from the fat is less than 30 minutes.

13. The method of claim 12, wherein the total time for sterilely extracting stem cells from the fat is less than 10 minutes.

14. The apparatus of claim 1, wherein the specimen container has an outer wall and a constant volume inside the outer wall.

15. The apparatus of claim 1, wherein the specimen container has a single lumen.

16. The apparatus of claim 1, wherein the specimen container comprises a plastic.

17. A method for extracting stem cells from fat, the method comprising:
- placing an agitator cap onto an open end of a specimen container having an open end and closed bottom, the agitator cap being removably coupled to the specimen container and also coupled to a mechanical agitator;
- separating stem cells from fat in a specimen container by the mechanical agitator in an operating sterile room;
- replacing the agitator cap with an aspiration cap onto the open end of the specimen container, the aspiration cap being removably coupled to the specimen container and also coupled to a syringe configured for extracting samples from the specimen container;
- placing the specimen container with the aspiration cap in a centrifuge to concentrate the separated stem cells;
- removing the specimen container from the centrifuge; and
- extracting the stem cells from the bottom of the specimen container, wherein the specimen retains sterility through the sequence of the above steps.

18. The method of claim 17, wherein the aspiration cap comprises an air inlet for the specimen container.

19. The method of claim 17, wherein the specimen container has a single lumen.

20. The method of claim 17, wherein the specimen container has an outer wall and a constant volume inside the outer wall.

* * * * *